(12) United States Patent
Deschler et al.

(10) Patent No.: US 7,323,582 B2
(45) Date of Patent: Jan. 29, 2008

(54) ORGANOSILICON COMPOUNDS

(75) Inventors: Ulrich Deschler, Sailauf (DE); Roland Krafczyk, Rheinfelden (DE); Hans-Detlef Luginsland, Cologne (DE); Karsten Korth, Wyhlen (DE); Ingo Kiefer, Schopfheim (DE); Michael Horn, Rheinfelden (DE)

(73) Assignee: Degussa AG, Duesseldorf (DE)

( * ) Notice: Subject to any disclaimer, the term of this patent is extended or adjusted under 35 U.S.C. 154(b) by 185 days.

(21) Appl. No.: 10/902,572

(22) Filed: Jul. 30, 2004

(65) Prior Publication Data

US 2005/0004386 A1      Jan. 6, 2005

Related U.S. Application Data

(62) Division of application No. 10/212,220, filed on Aug. 6, 2002, now Pat. No. 6,849,754.

(30) Foreign Application Priority Data

| Aug. 6, 2001 | (DE) | ................................. 101 37 809 |
| Dec. 22, 2001 | (DE) | ................................. 101 63 941 |
| May 24, 2002 | (DE) | ................................. 102 23 073 |

(51) Int. Cl.
| C07F 7/04 | (2006.01) |
| C07F 7/08 | (2006.01) |
| C08G 77/06 | (2006.01) |
| C07G 77/48 | (2006.01) |
| C07G 77/60 | (2006.01) |

(52) U.S. Cl. .................. 556/427; 556/429; 556/436; 556/437; 556/442; 528/18

(58) Field of Classification Search .................... None
See application file for complete search history.

(56) References Cited

U.S. PATENT DOCUMENTS

| 3,133,111 A | 5/1964 | Wheeler |
| 4,039,567 A | 8/1977 | Koetzsch et al. |
| 4,129,585 A | 12/1978 | Buder et al. |
| 4,179,537 A | 12/1979 | Rykowski |
| 4,506,087 A | 3/1985 | Fischer et al. |
| 5,518,699 A | 5/1996 | Kashnitz et al. |

FOREIGN PATENT DOCUMENTS

| DE | 15 45 080 | 8/1969 |
| DE | 24 27 085 | 12/1975 |
| DE | 25 38 341 | 3/1976 |
| DE | 27 12 866 A1 | 9/1978 |
| DE | 34 26 987 | 1/1986 |
| EP | 0 085 831 | 8/1983 |
| EP | 0 107 765 | 5/1984 |
| EP | 0 633 048 | 1/1995 |
| EP | 0 785 206 | 7/1997 |
| EP | 0 787 773 | 8/1997 |
| EP | 1 368 359 | 12/2003 |
| FR | 1 590 402 | 5/1970 |
| GB | 1 500 363 | * 8/1978 |
| JP | 2-160792 | 6/1990 |
| JP | 5-271250 | 10/1993 |
| JP | 2002-145890 | 5/2002 |
| SU | 1155602 | 1/1983 |
| WO | WO 02/08333 | 1/2002 |

OTHER PUBLICATIONS

Database CAPLUS on STN, Acc. No. 1976:44342, Pletka et al., DE 2405758 (Aug. 21, 1975) (abstract).*
Chemical Abstracts, WO 2002/008333, Jan. 31, 2002.
Database CAPLUS on STN, Acc. No. 1984:175849, JP 58164604 (Sep. 29, 1983) (abstract).
Database CAPLUS on STN, Acc. No. 1988:114012, Hirata et al., JP 62181346 Aug. 8, 1987 (abstract).
K. Dorgham et al., Database Crossfire Beilstein Online!, Phys. Chim. Biol., vol. 85, No. 5, XP-002265845, 2 pp., Database ascession No. BRN 6563251, 1988.
Braun, Database Crossfire Beilstein Online!, Inorg. Chem., vol. 5, 2 pp., XP-002265844, Database accession No. BRN 2304297, 1966.
Heidrun Steimann et al., "Umalkoxylierung in der siliciumorganischen Chemie", Z. Chem, 17, Jg. (1977) Heft.3, pp. 89-92 (w.English translation).

* cited by examiner

*Primary Examiner*—Brian Davis
(74) *Attorney, Agent, or Firm*—Oblon, Spivak, McClelland, Maier & Neustadt, P.C.

(57) ABSTRACT

Organosilicon compounds of the general formula I and/or II

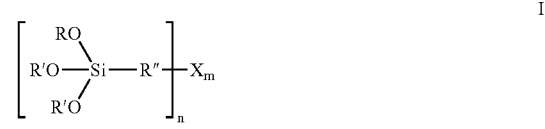

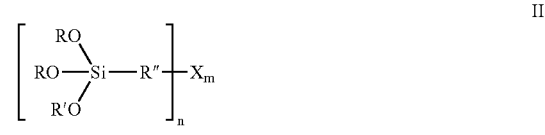

are produced by reacting silanes of the general formula III

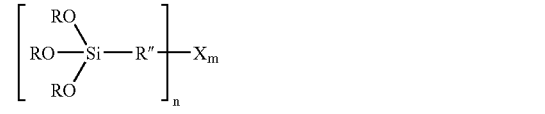

with alcohols of the general formula R'—OH, with elimination of R—OH, wherein R—OH may be continuously separated from the reaction mixture by distillation. The organosilicon compounds may be used in rubber mixtures. Compounds, such as rubbers, produced using such organosilicon compounds.

37 Claims, No Drawings

ORGANOSILICON COMPOUNDS

CROSS-REFERENCE TO RELATED APPLICATIONS

This application is a divisional of application Ser. No. 10/212,220, filed Aug. 6, 2002, now U.S. Pat. No. 6,849,754.

CROSS-REFERENCE TO RELATED APPLICATIONS

This application is related to and claims priority to DE 101 37 809 2, filed Aug. 6, 2001; DE 101 63 941.4, filed Dec. 22, 2001; and DE 10223 073.0, filed May 24, 2002. The contents of these applications is hereby incorporated by reference in their entirety.

BACKGROUND OF THE INVENTION

1. Field of the Invention

This invention relates to organosilicon compounds, to a process for the production thereof and to the use thereof.

2. Description of the Related Art

It is known to use silanes as adhesion promoters. Aminoalkyltrialkoxysilanes, such as for example 3-aminopropyltrimethoxysilane and 3-aminopropyltriethoxysilane, methacryloxyalkyltrialkoxysilanes, such as for example 3-methacryloxypropyltrimethoxysilane, polysulfane alkyltrialkoxysilanes, such as for example bis[3-triethoxysilylpropyl]polysulfane and bis[3-triethoxysilylpropyl]disulfane and mercaptoalkyltrialkoxysilanes, such as for example 3-mercaptopropyltrimethoxysilane and 3-mercaptopropyltriethoxysilane as adhesion promoters between inorganic materials, for example glass fibres, metals or oxide fillers, and organic polymers, such as thermosets, thermoplastics and elastomers, or as crosslinking agents and surface-modifying agents.

These adhesion promoters or coupling or bonding agents form bonds both with the filler and with the elastomer, so ensuring good interaction between the filler surface and the elastomer. They reduce mixture viscosity and facilitate filler dispersion.

It is moreover known that using conventional commercial silane adhesion promoters (DE 22 55 577) having three alkoxy substituents on the silicon atom results in the release of considerable quantities of alcohol during and after bonding to the filler. Since the silanes used are generally trimethoxy- and triethoxy-substituted, considerable quantities of the corresponding alcohols methanol and ethanol are released.

It is furthermore known that methoxy- and ethoxy-substituted silanes are more reactive than the corresponding long-chain alkoxy-substituted silanes and are thus able to bond themselves to the filler more rapidly, such that, on economic grounds, it is not possible to dispense with the use of methoxy- and ethoxy-substituted silanes.

One disadvantage of known organosilicon compounds is the release of volatile alcohols, such as methanol and ethanol, into the environment during and after bonding of the silane to the filler.

BRIEF DESCRIPTION OF THE INVENTION

One object of the invention is the production of organosilicon compounds which release smaller quantities of volatile alcohol during bonding to a filler, such as an inorganic filler.

Another object of the invention is the production of organosilicon compounds having elevated reactivity with either a filler or a compound, such as an organic polymer.

Advantageously the invention provides an organosilicon compound which releases smaller quantities of substances, such as volatile alcohols during bonding, as well as simultaneously providing elevated reactivity during bonding.

Still other objects of the invention will be evident from the following description.

DETAILED DESCRIPTION OF THE INVENTION

The present invention provides organosilicon compounds of the general formula I and/or II:

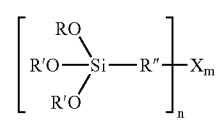

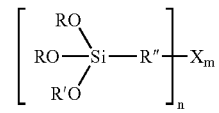

wherein R is a methyl or ethyl group,

R' is identical or different and is a $C_9$-$C_{30}$ branched or unbranched monovalent alkyl or alkenyl group, aryl group, aralkyl group, branched or unbranched $C_2$-$C_{30}$ alkyl ether group, branched or unbranched $C_2$-$C_{30}$ alkyl polyether group or R'''$_3$Si, where R''' is $C_1$-$C_{30}$ branched or unbranched alkyl or alkenyl group, aralkyl group or aryl group, R" is a branched or unbranched, saturated or unsaturated, aliphatic, aromatic or mixed aliphatic/aromatic divalent $C_1$-$C_{30}$ hydrocarbon group, X is $NH_{(3-n)}$ where n=1, 2, 3 and m=1, O(C=O)—R''' where n=1 and m=1, SH where n=1 and m=1, S where n=2 and m=1-10 and mixtures thereof, S(C=O)—R''' where n=1 and m=1 or H where n=1 and m=1.

R" may mean $CH_2$, $CH_2CH_2$, $CH_2CH_2CH_2$, $CH_2CH_2CH_2CH_2$, $CH(CH_3)$, $CH_2CH(CH_3)$, $C(CH_3)_2$, $CH(C_2H_5)$, $CH_2CH_2CH(CH_3)$, $CH_2CH(CH_3)CH_2$ or

Organosilicon compounds according to the invention of the formula I or II may be:

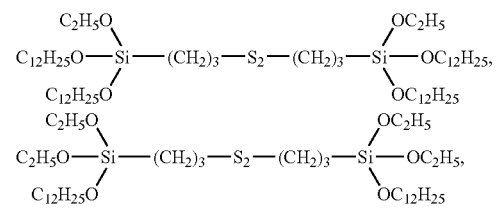

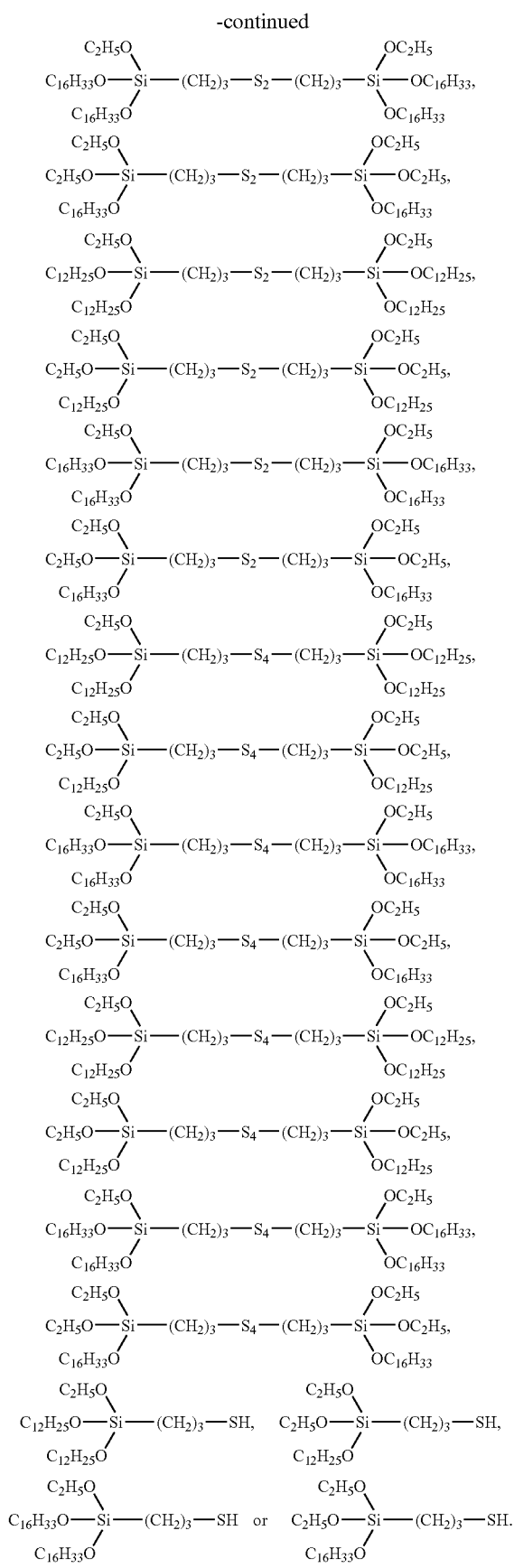

The present invention also provides a process for the production of the organosilicon compounds according to the invention, which process is characterised in that silanes of the general formula III:

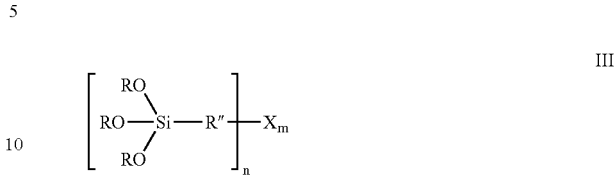

in which R, R'', X, m and n have the above-stated meaning, are reacted with alcohols of the general formula R'—OH, in which R' exhibits the above-stated meaning, with elimination of R—OH. R—OH may be continuously separated from the reaction mixture by distillation.

In the process according to the invention, a mixture may be obtained in which none, one, two or three of the RO groups are replaced by R'O groups. The ratio of the RO groups to R'O groups may be determined by the molar ratio of the silane of the general formula III to the alcohol of the general formula R'—OH. For example, when n=1, an organosilicon compound having an average composition according to the formula I may be produced by reacting two mol equivalents of the alcohol of the general formula R'—OH with one mol equivalent of the silane of the general formula III. For example, when n=2, an organosilicon compound having an average composition according to the formula I may be produced by reacting four mol equivalents of the alcohol of the general formula R'—OH with one mol equivalent of the silane of the general formula III.

The mixture may be used as is or separated into individual compounds.

When R'=R'''$_3$Si, the silane of the general formula III may be reacted with R'''$_3$Si—OH or with R'''$_3$Si—O—SiR'''$_3$. The compound R'''$_3$Si—O—SiR'''$_3$ can hydrolyse to yield R'''$_3$Si—OH and react with the silane of the general formula III.

The reaction may be accelerated by neutral, acidic or basic catalysts, such as hydrochloric acid, sulfuric acid, phosphoric acid, formic acid, acetic acid, para-toluene-sulfonic acid, sodium hydroxide solution, potassium hydroxide solution, sodium methylate, sodium ethylate, Deloxan ASP I/9, Amberlyst 15 ion exchange resins or metal compounds.

Metal compounds may also be transition metal compounds.

Metal compounds which may be used for the catalysts are metal chlorides, metal oxides, metal oxychlorides, metal alkoxides, metal oxyalkoxides, metal amides, metal imides or transition metal compounds with multiple, bound ligands. The following may, for example, be used as metal compounds: halides, amides or alkoxides main group 3 ($M^{3+}$=B, Al, Ga, In, Tl: $M^{3+}(OMe)_3$, $M^{3+}(OEt)_3$, $M^{3+}(OC_3H_7)_3$, $M^{3+}(OC_4H_9)_3$), halides, oxides, imides, alkoxides, amides, thiolates and combinations of the stated classes of substituents with multiple, bound ligands on compounds of the lanthanide group (rare earths, atomic numbers 58 to 71 in the periodic system of elements), halides, oxides, imides, alkoxides, amides, thiolates and combinations of the stated classes of substituents with multiple, bound ligands on compounds of subgroup 3 ($M^{3+}$=Sc, Y, La: $M^{3+}(OMe)_3$, $M^{3+}(OEt)_3$, $M^{3+}(OC_3H_7)_3$, $M^{3+}(OC_4H_9)_3$, cp$M^{3+}(Cl)_2$, Cp cp$M^{3+}(OMe)_2$, cp$M^{3+}(OEt)_2$, cp$M^{3+}(NMe_2)_2$ where cp=cyclopentadienyl), halides, amides, thiolates or alkoxides of main group 4 ($M^{4+}$=Si, Ge, Sn, Pb: $M^{4+}(OMe)_4$, $M^{4+}(OEt)_4$, $M^{4+}(OC_3H_7)_4$, $M^{4+}(OC_4H_9)_4$; $M^{2+}$=Sn, Pb: $M^{2+}(OMe)_2$, $M^{2+}(OEt)_2$, $M^{2+}(OC_3H_7)_2$, $M^{2+}(OC_4H_9)_2$, tin dilaurate, tin diacetate, $Sn(OBu)_2$), halides, oxides, imides, alkoxides, amides, thiolates and combinations of the stated classes of substituents with multiple, bound ligands on compounds of subgroup 4 ($M^{4+}$=Ti, Zr, Hf: $M^{4+}(F)_4$, $M^{4+}(Cl)_4$, $M^{4+}(Br)_4$, $M^{4+}(I)_4$; $M^{4+}(OMe)_4$, $M^{4+}(OEt)_4$, $M^{4+}(OC_3H_7)_4$, $M^{4+}(OC_4H_9)_4$, $cp_2Ti(Cl)_2$, $cp_2Zr(Cl)_2$, $cp_2Hf(Cl)_2$, $cp_2Ti(OMe)_2$, $cp_2Zr(OMe)_2$, $cp_2Hf(OMe)_2$, $cpTi(Cl)_3$, $cpZr(Cl)_3$, $cpHf(Cl)_3$; $cpTi(OMe)_3$, $cpZr(OMe)_3$, $cpHf(OMe)_3$, $M^{4+}(NMe_2)_4$, $M^{4+}(NEt_2)_4$, $M^{4+}(NHC_4H_9)_4$), halides, oxides, imides, alkoxides, amides, thiolates and combinations of the stated classes of substituents with multiple, bound ligands on compounds of subgroup 5 ($M^{5+}$, $M^{4+}$ or $M^{3+}$=V, Nb, Ta: $M^{5+}(OMe)_5$, $M^{5+}(OEt)_5$, $M^{5+}(OC_3H_7)_5$, $M^{5+}(OC_4H_9)_5$, $M^{3+}O(OMe)_3$, $M^{3+}O(OEt)_3$, $M^{3+}O(OC_3H_7)_3$, $M^{3+}O(OC_4H_9)_3$, $cpV(OMe)_4$, $cpNb(OMe)_3$, $cpTa(OMe)_3$; $cpV(OMe)_2$, $cpNb(OMe)_3$, $cpTa(OMe)_3$), halides, oxides, imides, alkoxides, amides, thiolates and combinations of the stated classes of substituents with multiple, bound ligands on compounds of subgroup 6 ($M^{6+}$, $M^{5+}$ or $M^{4+}$=Cr, Mo, W: $M^{6+}(OMe)_6$, $M^{6+}(OEt)_6$, $M^{6+}(OC_3H_7)_6$, $M^{6+}(OC_4H_9)_6$, $M^{6+}O(OMe)_4$, $M^{6+}O(OEt)_4$, $M^{6+}O(OC_3H_7)_4$, $M^{6+}O(OC_4H_9)_4$, $M^{6+}O_2(OMe)_2$, $M^{6+}O_2(OEt)_2$, $M^{6+}O_2(OC_3H_7)_2$, $M^{6+}O_2(OC_4H_9)_2$, $M^{6+}O_2(OSiMe_3)_2$) or halides, oxides, imides, alkoxides, amides, thiolates and combinations of the stated classes of substituents with multiple, bound ligands on compounds of subgroup 7 ($M^{7+}$, $M^{6+}$, $M^{5+}$ or $M^{4+}$=Mn, Re: $M^{7+}O(OMe)_5$, $M^{7+}O(OEt)_5$, $M^{7+}O(OC_3H_7)_5$, $M^{7+}O(OC_4H_9)_5$, $M^{7+}O_2(OMe)_3$, $M^{7+}O_2(OEt)_3$, $M^{7+}O_2(OC_3H_7)_3$, $M^{7+}O_2(OC_4H_9)_3$, $M^{7+}O_2(OSiMe_3)_3$, $M^{7+}O_3(OSiMe_3)$, $M^{7+}O_3(CH_3)$).

The metal compounds may have a free coordination site on the metal.

Metal compounds which are formed by addition of water to yield hydrolysable metal compounds may also be used as catalysts.

In one particular embodiment, titanates, such as for example tetra-n-butyl orthotitanate or tetra-iso-propyl orthotitanate, may be used as catalysts.

The metal compounds may be anhydrous, as a result of which overall less water is introduced into the reaction mixture and fewer oligomeric silane compounds are obtained.

The reaction may be performed at temperatures of between 20 and 200° C. This range includes all intermediate values, for instance, 21, 22, 25, 30, 40, 50, 75, 100, 125, 150, 175, 180, 190, 195, 198 or 199° C. In order to avoid condensation reactions, it may be advantageous to perform the reaction in an anhydrous atmosphere, preferably in an inert gas atmosphere.

The organosilicon compounds according to the invention may be used as adhesion promoters between inorganic materials (for example glass fibers, metals, oxide fillers, silicas) and organic polymers (for example thermosets, thermoplastics, elastomers), or as crosslinking agents and surface-modifying agents. The organosilicon compounds according to the invention may be used as adhesion promoters in tires filled with silica and/or starch.

The present invention also provides rubber mixtures, which are characterised in that they contain rubber, filler, such as for example precipitated silica, optionally further rubber auxiliary substances, as well as at least one organosilicon compound according to the invention.

The organosilicon compound according to the invention may be used in rubber or synthetic rubber mixtures, for instance, in quantities of 0.1 to 20 wt. %, relative to the quantity of rubber used. This range includes all intermediate values, such as 0.2%, 0.3%, 0.5%, 1%, 2%, 5%, 10%, 12.5% or 15%.

The organosilicon compounds according to the invention and the fillers may preferably be added at composition temperatures of 100 to 200° C. This range includes all intermediate values, such 101, 102, 105, 110, 115, 120, 125, 130, 140, 150, 160, 170, 180, 190, 195, or 199° C. They may, however, also be added later at lower temperatures (40 to 100° C. or any intermediate value within this range), for example together with further rubber auxiliary substances.

The organosilicon compound may be added to the mixing process both in pure form and applied onto an inert organic or inorganic support. Preferred support materials are silicas, waxes, thermoplastics, natural or synthetic silicates, aluminium oxide or carbon blacks.

The following fillers may be used as fillers for the rubber mixtures according to the invention:

carbon blacks: the carbon blacks to be used for this purpose are produced using the lamp black, furnace black or gas black processes and have BET surface areas of 20 to 200 $m^2/g$, such as for example SAF, ISAF, HSAF, HAF, FEF or GPF blacks. The carbon blacks may optionally also contain heteroatoms such as for example Si.

highly disperse silicas produced, for example, by precipitation of solutions of silicates or flame hydrolysis of silicon halides, with specific surface areas of 5 to 1000, preferably of 20 to 400 $m^2/g$ (BET surface area) and with primary particle sizes of 10 to 400 nm. The silicas may optionally also assume the form of mixed oxides with other metal oxides, such as Al, Mg, Ca, Ba, Zn and titanium oxides.

synthetic silicates, such as aluminium silicate, alkaline earth metal silicates, such as magnesium silicate or calcium silicate, with BET surface areas of 20 to 400 $m^2/g$ and primary particle diameters of 10 to 400 nm.

synthetic or natural aluminium oxides and hydroxides.

natural silicates, such as kaolin and other naturally occurring silicas.

glass fibres and glass fibre products (mats, strands) or glass microbeads.

Highly disperse silicas, produced by precipitation of solutions of silicates, with BET surface areas of 20 to 400 $m^2/g$ may preferably be used in quantities of 5 to 150 parts by weight, in each case relative to 100 parts of rubber.

The stated fillers may be used individually or as a mixture. In a particularly preferred embodiment of the process, 10 to 150 parts by weight of light-coloured fillers, optionally together with 0 to 100 parts by weight of carbon black, and 0.3 to 10 parts by weight of a compound of the oligomeric organosilanes according to the invention, in each case relative to 100 parts by weight of rubber, may be used to produce the mixtures.

Not only natural rubber but also synthetic rubbers are suitable for the production of the rubber mixtures according to the invention. Preferred synthetic rubbers are described, for example, in W. Hofmann, Kautschuk-technologie, Genter Verlag, Stuttgart 1980. They include, inter alia, polybutadiene (BR)
polyisoprene (IR)
styrene/butadiene copolymers with styrene contents of 1 to 60, preferably of 2 to 50 wt. % (SBR)
isobutylene/isoprene copolymers (IIR)
butadiene/acrylonitrile copolymers with acrylonitrile contents of 5 to 60, preferably of 10 to 50 wt. % (NBR)

partially hydrogenated or completely hydrogenated NBR rubber (HNBR)

ethylene/propylene/diene copolymers (EPDM)

as well as mixtures of these rubbers. Anionically polymerised S-SBR rubbers (solution SBR) with a glass transition temperature of above −50° C. and the mixtures thereof with diene rubbers are in particular of interest for the production of automotive tyres.

The rubber vulcanisates according to the invention may contain further rubber auxiliary substances, such as reaction accelerators, antioxidants, heat stabilisers, light stabilisers, antiozonants, processing auxiliaries, plasticisers, tackifiers, blowing agents, dyes, pigments, waxes, extenders, organic acids, retarders, metal oxides as well as activators, such as triethanolamine, polyethylene glycol, hexanetriol, which are known in the rubber industry.

The rubber auxiliary substances may be used in known quantities which are determined, inter alia, by the intended application. Conventional quantities are for example quantities of 0.1 to 50 wt. % (or any intermediate value within this range, e.g. 0.2, 0.5, 1, 5, 10, 20, 30, 40, 45 or 49%), relative to rubber. Sulfur or sulfur-donating substances may be used as vulcanising agents. The rubber mixtures according to the invention may furthermore contain vulcanisation accelerators. Examples of suitable vulcanisation accelerators are mercaptobenzothiazoles, sulfenamides, guanidines, thiurams, dithiocarbamates, thioureas and thiocarbonates. The vulcanisation accelerators and sulfur are used in quantities of 0.1 to 10 wt. %, preferably of 0.1 to 5 wt. %, relative to rubber.

Vulcanisation of the rubber mixtures according to the invention may proceed at temperatures of 100 to 200° C. (or at any intermediate value within this range, e.g. 101, 102, 105, 110, 120, 130, 140, 150, 160, 170, 180, 190, 195, or 199° C.), preferably of 130 to 180° C., optionally under a pressure of 10 to 200 bar. Blending of the rubbers with the filler, optionally rubber auxiliary substances and the organosilicon compound according to the invention may be performed in known mixing units, such as roll mills, internal mixers and compounding extruders.

The rubber mixtures according to the invention are suited to the production of mouldings, for example for the production of pneumatic tires, tire treads, cable sheathing, hoses, drive belts, conveyor, roll covers, tires, shoe soles, sealing rings, and damping components.

The organosilicon compounds according to the invention have the advantage that, at constant reactivity, less methanol or ethanol is released than with known silanes. Due to their inactivity, the nonvolatile alcohols are not separated from the silane or, due to their nonvolatility, remain in the polymer matrix. In either case, they are not released into the environment.

EXAMPLE 1

200.0 g of bis(3-triethoxysilylpropyl)polysulfane (formula III where R=ethyl, R"=$CH_2CH_2CH_2$, X=S, n=2 and m=3.8) and 70.0 g of 1-dodecanol (R'=$C_{12}H_{25}$) are initially introduced at room temperature into a 1 liter four-necked flask with distillation attachment and combined with 1.0 g of Amberlyst 15. The yellowish solution is heated to 100-130° C., the resultant ethanol removed by distillation and 210 g of 1-dodecanol are added dropwise within 1.5 h. The resultant ethanol is continuously removed by distillation. Towards the end of the reaction, the temperature is briefly raised to 150° C. The mixture is then distilled in a rotary evaporator under a vacuum at 80° C. and 50 mbar. 408.5 g (99.4%) of a yellow liquid of the formula I where R=ethyl, R'=$C_{12}H_{25}$, R"=$CH_2CH_2CH_2$, X=S, n=2 and m=3.8 are obtained.

EXAMPLE 2

200.0 g of bis(3-triethoxysilylpropyl)polysulfane (formula III where R=ethyl, R"=$CH_2CH_2CH_2$, X=S, n=2 and m=3.8) and 70.0 g of 1-dodecanol (R'=$C_{12}H_{25}$) are initially introduced at room temperature into a 1 liter four-necked flask with distillation attachment and combined with 0.7 g of p-toluenesulfonic acid monohydrate. The yellowish solution is heated to 100-105° C., the resultant ethanol removed by distillation and 210 g of 1-dodecanol are added dropwise within 1.5 h. The resultant ethanol is continuously removed by distillation. Towards the end of the reaction, the temperature is briefly raised to 130° C. The mixture is then distilled in a rotary evaporator under a vacuum at 80° C. and 50 mbar. 389.1 g (94.7%) of a yellow liquid of the formula I where R=ethyl, R'=$C_{12}H_{25}$, R"=$CH_2CH_2CH_2$, X=S, n=2 and m=3.8 are obtained.

EXAMPLE 3

200.0 g of bis(3-triethoxysilylpropyl)polysulfane (formula III where R=ethyl, R"=$CH_2CH_2CH_2$, X=S, n=2 and m=3.8) and 60.6 g of diethylene glycol monobutyl ether (R'=$(CH_2)_2$—O—$(CH_2)_2$—O—$C_4H_9$) are initially introduced at room temperature into a 1 liter four-necked flask with distillation attachment and combined with 1.0 g of Amberlyst 15. The yellowish solution is heated to 115-130° C., the resultant ethanol removed by distillation and 183.2 g of diethylene glycol monobutyl ether are added dropwise within 1.5 h. The resultant ethanol is continuously removed by distillation. The mixture is then distilled in a rotary evaporator under a vacuum at 80° C. and 25 mbar. 367.2 g (98.2%) of a yellow liquid of the formula I where R=ethyl, R'=$(CH_2)_2$—O—$(CH_2)_2$—O—$C_4H_9$, R"=$CH_2CH_2CH_2$, X=S, n=2 and m=3.8 are obtained.

EXAMPLE 4

200.0 g of bis(3-triethoxysilylpropyl)polysulfane (formula III where R=ethyl, R"=$CH_2CH_2CH_2$, X=S, n=2 and m=3.8) and 60.9 g of diethylene glycol monobutyl ether (R'=$(CH_2)_2$—O—$(CH_2)_2$—O—$C_4H_9$) are initially introduced at room temperature into a 1 liter four-necked flask with distillation attachment and combined with 0.7 g of p-toluenesulfonic acid monohydrate. The yellowish solution is heated to 120-130° C., the resultant ethanol removed by distillation and 182.8 g of diethylene glycol monobutyl ether are added dropwise within 1.5 h. The resultant ethanol is continuously removed by distillation. The mixture is then distilled in a rotary evaporator under a vacuum at 80° C. and 20 mbar. 358.5 g (95.1%) of a yellow liquid of the formula I where R=ethyl, R'=$(CH_2)_2$—O—$(CH_2)_2$—O—$C_4H_9$, R"=$CH_2CH_2CH_2$, X=S, n=2 and m=3.8 are obtained.

EXAMPLE 5

200.0 g of bis(3-triethoxysilylpropyl)polysulfane (formula III where R=ethyl, R"=$CH_2CH_2CH_2$, X=S, n=2 and m=3.8) and 80.5 g of 1-tetradecanol (R'=$C_{14}H_{29}$) are initially introduced at room temperature into a 1 liter four-necked flask with distillation attachment and combined with 0.7 g of p-toluenesulfonic acid monohydrate. The yellowish solution is heated to 120-130° C., the resultant ethanol removed by distillation and 241.7 g of tetradecanol are added within 2 h. The resultant ethanol is continuously removed by distillation. The mixture is then distilled in a rotary evaporator under a vacuum at 80° C. and 20 mbar. 432.1 g (95.4%) of a yellow liquid of the formula I where R=ethyl, R'=$C_{14}H_{29}$, R"=$CH_2CH_2CH_2$, X=S, n=2 and m=3.8 are obtained.

EXAMPLE 6

200.0 g of bis(3-triethoxysilylpropyl)polysulfane (formula III where R=ethyl, R"=$CH_2CH_2CH_2$, X=S, n=2 and m=3.8) and 80.5 g of 1-tetradecanol (R'=—$C_{14}H_{29}$) are initially introduced at room temperature into a 1 liter four-necked flask with distillation attachment and combined with 1.0 g of Deloxan ASP I/9 from Degussa. The yellowish solution is heated to 120-130° C., the resultant ethanol removed by distillation and 241.7 g of tetradecanol are added within 2 h. The resultant ethanol is continuously removed by distillation. The mixture is then distilled in a rotary evaporator under a vacuum at 80° C. and 20 mbar. 448.3 g (99.0%) of a yellow liquid of the formula I where R=ethyl, R'=—$C_{14}H_{29}$, R"=$CH_2CH_2CH_2$, X=S, n=2 and m=3.8 are obtained.

EXAMPLE 7

200.0 g of bis(3-triethoxysilylpropyl)polysulfane (formula III where R=ethyl, R"=$CH_2CH_2CH_2$, X=S, n=2 and m=3.8) and 50.4 g of diethylene glycol monoethyl ether (R'=$(CH_2)_2$—O—$(CH_2)_2$—O—$C_2H_5$) are initially introduced at room temperature into a 1 liter four-necked flask with distillation attachment and combined with 0.7 g of p-toluenesulfonic acid monohydrate. The yellowish solution is heated to 125-130° C., the resultant ethanol removed by distillation and 151.2 g of diethylene glycol monoethyl ether are added dropwise within 1.5 h. The resultant ethanol is continuously removed by distillation. The mixture is then distilled in a rotary evaporator under a vacuum at 80° C. and 25 mbar. 321.9 g (96.6%) of a yellow liquid of the formula I where R=ethyl, R'=$(CH_2)_2$—O—$(CH_2)_2$—O—$C_2H_5$, R"=$CH_2CH_2CH_2$, X=S, n=2 and m=3.8 are obtained.

EXAMPLE 8

200.0 g of bis(3-triethoxysilylpropyl)polysulfane (formula III where R=ethyl, R"=$CH_2CH_2CH_2$, X=S, n=2 and m=3.8) and 50.4 g of diethylene glycol monoethyl ether (R'=$(CH_2)_2$—O—$(CH_2)_2$—O—$C_2H_5$) are initially introduced at room temperature into a 1 liter four-necked flask with distillation attachment and combined with 1.0 g of Amberlyst 15. The yellowish solution is heated to 125° C., the resultant ethanol removed by distillation and 151.2 g of diethylene glycol monoethyl ether are added dropwise within 1.5 h. The resultant ethanol is continuously removed by distillation. The mixture is then distilled in a rotary evaporator under a vacuum at 80° C. and 25 mbar. 321.9 g (96.9%) of a yellow liquid of the formula I where R=ethyl, R'=$(CH_2)_2$—O—$(CH_2)_2$—O—$C_2H_5$, R"=$CH_2CH_2CH_2$, X=S, n=2 and m=3.8 are obtained.

EXAMPLE 9

200.0 g of bis(3-triethoxysilylpropyl)polysulfane (formula III where R=ethyl, R"=$CH_2CH_2CH_2$, X=S, n=2 and m=3.8) and 71.8 g of diethylene glycol monohexyl ether (R'=$(CH_2)_2$—O—$(CH_2)_2$—O—$C_6H_{13}$) are initially introduced at room temperature into a 1 liter four-necked flask with distillation attachment and combined with 0.7 g of p-toluenesulfonic acid monohydrate. The yellowish solution is heated to 125° C., the resultant ethanol removed by distillation and 214.2 g of diethylene glycol monohexyl ether are added within 1.5 h. The resultant ethanol is continuously removed by distillation. The mixture is then distilled in a rotary evaporator under a vacuum at 80° C. and 25 mbar. 414.4 g (99.4%) of a yellow liquid of the formula I where R=ethyl, R'=$(CH_2)_2$—O—$(CH_2)_2$—O—$C_6H_{13}$, R"=$CH_2CH_2CH_2$, X=S, n=2 and m=3.8 are obtained.

EXAMPLE 10

125.2 g of 3-mercaptopropyltriethoxysilane (formula III where R=—$CH_2CH_3$, R"=—$CH_2CH_2CH_2$—, X=—SH, n=1, m=1) and 22.5 g of 1-tetradecanol (R'=—$C_{14}H_{29}$) are initially introduced at room temperature into a 1 liter four-necked flask with distillation attachment and combined with 1.0 g of p-toluenesulfonic acid monohydrate. The solution is heated to 120° C. and, as soon as the resultant ethanol begins to distil off, 202.6 g of tetradecanol are added within 1.5 h. The resultant ethanol is continuously removed by distillation. The mixture is then distilled in a rotary evaporator under a vacuum at 80° C. and 20 mbar. 298.8 g (98.9%) of a colourless liquid of the type I where R=—$CH_2CH_3$, R'=—$C_{14}H_{29}$, R'=—$CH_2CH_2CH_2$—, X=—SH, n=1, m=1 are obtained.

EXAMPLE 11

Testing of the Organosilicon Compounds in Practical Rubber Applications

The formulation used for the rubber mixtures is stated in Table 1 below. The unit phr here means parts by weight relative to 100 parts of crude rubber used. The general method for the production of rubber mixtures and the vulcanisates thereof is described in the book "Rubber Technology Handbook", W. Hofmann, Hanser Verlag 1994.

TABLE 1

| | Mixture 1 Reference | Mixture 2 | Mixture 3 | Mixture 4 | Mixture 5 | Mixture 6 | Mixture 7 | Mixture 8 | Mixture 9 |
|---|---|---|---|---|---|---|---|---|---|
| 1st stage | | | | | | | | | |
| Buna VSL 5025-1 | 96 | 96 | 96 | 96 | 96 | 96 | 96 | 96 | 96 |
| Buna CB 24 | 30 | 30 | 30 | 30 | 30 | 30 | 30 | 30 | 30 |
| Ultrasil 7000 GR | 80 | 80 | 80 | 80 | 80 | 80 | 80 | 80 | 80 |
| Si69 | 6.4 | — | — | — | — | — | — | — | — |
| Example 1 | — | 13.01 | — | — | — | — | — | — | — |
| Example 2 | — | — | 13.35 | — | — | — | — | — | — |
| Example 3 | — | — | — | — | — | — | — | — | — |

TABLE 1-continued

|  | Mixture 1 Reference | Mixture 2 | Mixture 3 | Mixture 4 | Mixture 5 | Mixture 6 | Mixture 7 | Mixture 8 | Mixture 9 |
|---|---|---|---|---|---|---|---|---|---|
| Example 4 | — | — | — | 11.82 | — | — | — | — | — |
| Example 5 | — | — | — | — | 14.5 | — | — | — | — |
| Example 6 | — | — | — | — | — | 13.61 | — | — | — |
| Example 7 | — | — | — | — | — | — | 10.30 | — | — |
| Example 8 | — | — | — | — | — | — | — | 10.30 | — |
| Example 9 | — | — | — | — | — | — | — | — | 13.27 |
| ZnO | 3 | 3 | 3 | 3 | 3 | 3 | 3 | 3 | 3 |
| Stearic acid | 2 | 2 | 2 | 2 | 2 | 2 | 2 | 2 | 2 |
| Naftolen | 10 | 10 | 10 | 10 | 10 | 10 | 10 | 10 | 10 |
| Vulkanox 4020 | 1.5 | 1.5 | 1.5 | 1.5 | 1.5 | 1.5 | 1.5 | 1.5 | 1.5 |
| Protektor G35P | 1 | 1 | 1 | 1 | 1 | 1 | 1 | 1 | 1 |
| 2nd stage |  |  |  |  |  |  |  |  |  |
| Batch stage 1 |  |  |  |  |  |  |  |  |  |
| 3rd stage |  |  |  |  |  |  |  |  |  |
| Batch stage 2 |  |  |  |  |  |  |  |  |  |
| Vulkacit D | 2 | 2 | 2 | 2 | 2 | 2 | 2 | 2 | 2 |
| Vulkazit CZ | 1.5 | 1.5 | 1.5 | 1.5 | 1.5 | 1.5 | 1.5 | 1.5 | 1.5 |
| Sulfur | 1.5 | 1.5 | 1.5 | 1.5 | 1.5 | 1.5 | 1.5 | 1.5 | 1.5 |

Polymer VSL 5025-1 is a solution-polymerised SBR copolymer from Bayer AG with a styrene content of 25 wt. % and a butadiene content of 75 wt. %. The copolymer contains 37.5 phr of oil and exhibits a Mooney viscosity (ML 1+4/100° C.) of 50±4.

Polymer Buna CB 24 is a cis-1,4-polybutadiene (neodymium type) from Bayer AG having a cis-1,4 content of at least 97% and a Mooney viscosity of 44±5.

Naftolen ZD from Chemetall is used as the aromatic oil. Vulkanox 4020 is 6PPD from Bayer AG and Protektor G35P is an antiozonant wax from HB-Fuller GmbH. Vulkacit D (DPG) and Vulkazit CZ (CBS) are commercial products of Bayer AG.

Ultrasil 7000 GR is a readily dispersible precipitated silica from Degussa AG with a BET surface area of 170 m$^2$/g. Si 69, bis(3-triethoxysilylpropyl)tetrasulfane, is a commercial product of Degussa AG.

The rubber mixtures are produced in an internal mixer in accordance with the mixing instructions in Table 2.

TABLE 2

| Stage 1 | |
|---|---|
| Settings | |
| Mixing unit | Werner & Pfleiderer, type E |
| Rotor speed | 70 min$^{-1}$ |
| Ram pressure | 5.5 bar |
| Empty volume | 1.58 L |
| Fill level | 0.56 |
| Flow temp. | 80° C. |
| Mixing operation | |
| 0 to 1 min | Buna VSL 5025-1 + Buna CB 24 |
| 1 to 3 min | ½ filler, ZnO, stearic acid, Naftolen ZD, silane |
| 3 to 4 min | ½ filler, antioxidant |
| 4 min | Cleaning |
| 4 to 5 min | Mixing, possibly adjust rotor speed |
| 5 min | Discharge |
| Batch temp. | 145-150° C. |
| Storage | 24 h at room temperature |
| Stage 2 | |
| Settings | |
| Mixing unit | as in stage 1, except: |
| Rotor speed | 80 min$^{-1}$ |
| Fill level | 0.53 |
| Mixing operation | |
| 0 to 2 min | Break up batch from stage 1 |
| 2 to 5 min | Maintain batch temperature of 150° C. by varying rotor speed |
| 5 min | Discharge |
| Batch temp. | 150° C. |
| Storage | 4 h at room temperature |
| Stage 3 | |
| Settings | |
| Mixing unit | as in stage 1, except |
| Rotor speed | 40 min$^{-1}$ |
| Fill level | 0.51 |
| Flow temp. | 50° C. |
| Mixing operation | |
| 0 to 2 min | Batch from stage 2, accelerator, sulfur |
| 2 min | Discharge and sheet out on laboratory roll mill (diameter 200 mm, length 450 mm, flow temperature 50° C.) Homogenise: Cut and fold 3× left, 3× right and Run through mill 8× with narrow roller gap (1 mm) and 3× with large roller gap (3.5 mm) Sheet out |
| Batch temp. | 85-95° C. |

TABLE 3 summarises the rubber test methods.

| Physical testing | Standard/Conditions |
|---|---|
| ML 1 + 4, 100° C., 3rd stage | DIN 53523/3, ISO 667 |
| Vulcameter testing, 165° C. | DIN 53529/3, ISO 6502 |
| Dmax – Dmin (dNm) | |
| t10% and t90% (min) | |
| Tensile test on ring, 23° C. | DIN 53504, ISO 37 |
| Tensile strength (MPa) | |
| Modulus values (MPa) | |
| Elongation at break (%) | |
| Shore A hardness, 23° C. (SH) | DIN 53 505 |
| Viscoelastic properties, 0 to 60° C., 16 Hz, 50 N initial force and 25 N amplitude force | DIN 53 513, ISO 2856 |
| Complex modulus of elasticity E* (MPa) | |
| Loss factor, tan δ ( ) | |
| Ball rebound, 23° C. (%) | ASTM D 5308 |
| Goodrich Flexometer 0.25 inch stroke, 25 min, 23° C. | DIN 53 533, ASTM D 623 A |
| DIN abrasion, 10 N force (mm³) | DIN 53 516 |
| Dispersion ( ) | ISO/DIS 11345 |

The results from technical rubber testing are shown in Table 4a and Table 4b. The mixtures are vulcanised for 20 min at 165° C.

As is evident from the data in Tables 4a and 4b, the Mooney viscosity of the mixtures comprising the organosilicon compound according to the invention is below that of the reference mixture 1.

The mixtures comprising the organosilicon compounds according to the invention (ethers) exhibit more rapid vulcanisation. The reinforcement factor is at a high level for all the mixtures, while tensile strength and elongation at break values are likewise comparable with the Si 69 reference. DIN abrasion is good for all the mixtures. The static rubber values demonstrate that the silica-silane-rubber bond has formed.

The Goodrich Flexometer tests shows that the mixtures comprising the long-chain alcohols result in lower heat build-up and an improved permanent set. MTS testing clearly reveals lower dynamic rigidity values and a reduced tan δ 60° C. (lower rolling resistance).

EXAMPLE 12

180.0 g of bis(3-triethoxysilylpropyl)disulfane (formula III where R=Ethyl, R'''=$CH_2CH_2CH_2$, X=S, n=2 and m=2.2) and 80.5 g of 1-tetradecanol (R'=—$C_{14}H_{29}$) are initially introduced at room temperature into a 1 liter four-necked flask with distillation attachment and combined with 0.7 g of p-toluenesulfonic acid monohydrate. The yellowish solution

TABLE 4a

| | | Crude mixture results | | | | | | | | |
|---|---|---|---|---|---|---|---|---|---|---|
| Features | Unit | 1 | 2 | 3 | 4 | 5 | 6 | 7 | 8 | 9 |
| Batch temperature, 1st stage | [° C.] | 148 | 147 | 147 | 147 | 146 | 148 | 145 | 145 | 146 |
| Batch temperature, 2nd stage | [° C.] | 147 | 146 | 145 | 148 | 144 | 146 | 147 | 148 | 147 |
| ML(1 + 4) at 100° C., 3rd stage | [MU] | 62 | 46 | 47 | 52 | 45 | 45 | 58 | 58 | 49 |
| MDR, 165° C., 3° | | | | | | | | | | |
| $D_{max} - D_{min}$ | [dNm] | 15.74 | 13.54 | 13.38 | 15.26 | 13.25 | 13.23 | 15.35 | 15.62 | 14.95 |
| t 10% | [min] | 1.69 | 2 | 2.16 | 1.98 | 2.11 | 2.19 | 1.83 | 1.63 | 2 |
| t 20% | [min] | 3.12 | 3.2 | 3.53 | 3.37 | 3.45 | 3.5 | 3.16 | 2.85 | 3.36 |
| t 90% | [min] | 11.06 | 19.01 | 19.61 | 8.76 | 19.92 | 19.06 | 7.68 | 8.2 | 8.36 |
| t 80% – t 20% | [min] | 4.58 | 9.7 | 9.97 | 3.22 | 10.5 | 9.39 | 2.8 | 3.07 | 3.08 |

TABLE 4b

| | | Vulcanisate results | | | | | | | | |
|---|---|---|---|---|---|---|---|---|---|---|
| Feature | Unit | 1 | 2 | 3 | 4 | 5 | 6 | 7 | 8 | 9 |
| Tensile test, ring | | | | | | | | | | |
| Tensile strength | [MPa] | 11.5 | 13.4 | 12.7 | 13.9 | 11.9 | 12.1 | 14.7 | 14.7 | 13.1 |
| Modulus, 100% | [MPa] | 1.7 | 1.4 | 1.4 | 1.6 | 1.4 | 1.4 | 1.7 | 1.6 | 1.6 |
| Modulus, 300% | [MPa] | 8.8 | 7.7 | 7.6 | 8.0 | 7.4 | 7.7 | 8.4 | 8.2 | 7.7 |
| Modulus 300%/100% | [—] | 5.2 | 5.5 | 5.4 | 5.0 | 5.3 | 5.5 | 4.9 | 5.1 | 4.8 |
| Elongation at break | [%] | 360 | 430 | 420 | 440 | 400 | 400 | 440 | 450 | 430 |
| Shore A hardness | [SH] | 62 | 58 | 57 | 61 | 57 | 57 | 62 | 60 | 60 |
| Ball rebound, 60° C. | [%] | 59.4 | 65.2 | 65.0 | 61.3 | 65.3 | 65.3 | 61.4 | 61.4 | 63.3 |
| DIN abrasion | [mm³] | 56 | 60 | 55 | 65 | 55 | 53 | 65 | 63 | 53 |
| Goodrich Flexometer | | | | | | | | | | |
| Contact temperature | [° C.] | 63 | 57 | 59 | 59 | 60 | 57 | 60 | 62 | 54 |
| Puncture needle temperature | [° C.] | 112 | 104 | 106 | 101 | 108 | 103 | 101 | 106 | 96 |
| Permanent set | [%] | 6.5 | 3.8 | 4.2 | 5.9 | 3.2 | 3.6 | 4.7 | 5.5 | 3.8 |
| E*, 0° C. | [MPa] | 19.8 | 10.6 | 11.7 | 16.6 | 19.2 | 19 | 13.6 | 17 | 11.7 |
| E*, 60° C. | [MPa] | 7.8 | 6 | 6.4 | 7.3 | 6.1 | 5.9 | 7.2 | 7.7 | 6.7 |
| Loss factor, tanδ 0° C., | [—] | 0.476 | 0.351 | 0.354 | 0.452 | 0.462 | 0.468 | 0.391 | 0.447 | 0.354 |
| Loss factor, tanδ 60° C. | [—] | 0.104 | 0.089 | 0.093 | 0.096 | 0.099 | 0.092 | 0.088 | 0.099 | 0.084 |
| Phillips dispersion | [—] | 8 | 8 | 8 | 8 | 8 | 8 | 8 | 8 | 8 | is heated to 120-130° C., the resultant ethanol removed by distillation and 237.5 g of tetradecanol are added within 2 h. The resultant ethanol is continuously removed by distillation. The mixture is then distilled in a rotary evaporator under a vacuum at 80° C. and 20 mbar. 418.5 g (98.0%) of a yellow liquid of the formula I where R=ethyl, R'=—$C_{14}H_{29}$, R"=$CH_2CH_2CH_2$—, X=S, n=2 and m=2.2 are obtained.

EXAMPLE 13

A mixture of 125.2 g of 3-mercaptopropyltriethoxysilane (formula III where R=—$CH_2CH_3$, R"=—$CH_2CH_2CH_2$—, X=—SH, n=1, m=1), 225.1 g of 1-tetradecanol (R'=—$C_{14}H_{29}$) and 1.0 g of p-toluenesulfonic acid monohydrate are heated to 110° C. in the 1 liter flask on a rotary evaporator and the resultant ethanol removed by vacuum distillation at 40 mbar within 4 h. 298.5 g (98.8%) of a colourless liquid of the formula I where R=—$CH_2CH_3$, R'=—$C_{14}H_{29}$, R"=—$CH_2CH_2CH_2$—, X=—SH, n=1, m=1 are obtained.

EXAMPLE 14

A mixture of 200.0 g of bis(3-triethoxysilylpropyl)polysulfane (formula III where R=ethyl, R"=$CH_2CH_2CH_2$, X=S, n=2, m=3.8), 322.2 g of 1-tetradecanol (R'=—$C_{14}H_{29}$) and 1.0 g of p-toluenesulfonic acid monohydrate are heated to 110° C. in the 1 liter flask on a rotary evaporator and the resultant ethanol removed by vacuum distillation at 40 mbar within 4 h. 448.1 g (99.0%) of a yellow liquid of the formula I where R=ethyl, R'=—$C_{14}H_{29}$, R"=$CH_2CH_2CH_2$, X=S, n=2 and m=3.8 are obtained.

EXAMPLE 15

A mixture consisting of 150 g of Si 69 (compound III where R=—$CH_2CH_3$, $R^2$=—$CH_2CH_2CH_2$—, X=S, n=2, m=1 to 10 and an average m of 3.8), and a 4× molar quantity of tetradecanol are heated with the stated quantities of catalyst to the stated temperatures in the 1 liter flask on a rotary evaporator and the resultant ethanol is removed by vacuum distillation at 40 mbar within 120 min (Table 5). After cooling, a yellow to yellow-orange, relatively high viscosity liquid of the formula I where R=—$CH_2CH_3$, $R^2$=—$CH_2CH_2CH_2$—, X=S with n=2 and m=1 to 10 is obtained.

Si 69 is bis(3-triethoxysilylpropyl)polysulfane with an average sulfane chain length of 3.8 from Degussa AG.

$Ti(OC_2H_5)_4$, $Ti(OC_3H_7)_4$ and $Ti(OC_4H_9)_4$ are produced by Aldrich. p-Toluenesulfonic acid and p-toluenesulfonic acid sodium salt are produced by Merck-Schuchardt.

EXAMPLE 16

A mixture consisting of 100 g of Si 69 (compound III where R=—$CH_2CH_3$, $R^2$=—$CH_2CH_2CH_2$—, X=S, n=2, m=1 to 10 and an average m of 3.8), and a 4× molar quantity of corresponding alcohol are heated with the stated quantities of catalyst to 130° C. in a 500 ml three-necked flask and the resultant ethanol is removed by distillation within 120 min (Table 6). After cooling, a yellow to yellow-orange, relatively high viscosity liquid of the formula I where R=—$CH_2CH_3$, $R^2$=—$CH_2CH_2CH_2$—, X=S with n=2 and m=1 to 10 is obtained.

Tables 5 and 6 show the corresponding NMR analytical results.

The nuclear magnetic resonance analysis results are obtained using a Bruker DRX 500 NMR spectrometer in accordance with the rules and operating procedures known to the person skilled in the art. The mass frequencies used are 99.35 MHz for $^{29}$Si nuclei and 500 MHz for $^1$H nuclei.

Tetramethylsilane (TMS) is used as reference in each case.

Conversion is defined as the quotient obtained from the $^1$H NMR integral (Si—O—$C_xH_y$) divided by the sum of the $^1$H NMR integral (Si—O-Et) and $^1$H NMR integral (Si—O—$C_xH_y$)×0.66. Conversion is stated as a percentage of 1. 100% conversion means that 4 of 6 equivalents of EtO have been replaced and 2 equivalents of EtO remain on the silicon.

The quantity of oligomers is determined by $^{29}$Si NMR by comparing the integrals of the Si(OEt)$_3$ and the Si(OEt)$_2$-O—Si(OEt)$_2$ signals.

At a comparable or even lower molar catalyst concentration, the transesterification conversion of the process according to the invention using metal compounds is higher at lower temperatures than when other catalysts are used. In addition, the quantity of oligomers formed is lower. If p-toluenesulfonic acid sodium salt is used as an anhydrous equivalent of p-toluenesulfonic acid monohydrate, conversion is found to be poorer, even when large quantities of catalyst are used, than when titanium alkoxides are used (Table 6).

TABLE 5

| Alcohol | Catalyst | Quantity of catalyst (in each case equimolar) in g | Temperature ° C. | Time min | Transesterification conversion (4 OR' = 100%) | Quantity of oligomers (comparison of integrals from Si NMR, Si(OR)$_3$ = 100%; oligomers = x %) |
|---|---|---|---|---|---|---|
| Tetradecanol | Ti(OC$_4$H$_9$)$_4$ | 0.3 | 110 | 120 | >99 | 5.5 |
| Tetradecanol | Ti(OC$_4$H$_9$)$_4$ | 0.15 | 110 | 120 | >99 | 4.8 |
| Tetradecanol | Ti(OC$_4$H$_9$)$_4$ | 0.075 | 110 | 120 | 93 | 6.6 |
| Tetradecanol | p-toluenesulfonic acid monohydrate | 0.168 | 110 | 120 | 98 | 6.5 |
| Tetradecanol | p-toluenesulfonic acid monohydrate | 0.084 | 110 | 120 | 86 | 5.8 |
| Tetradecanol | p-toluenesulfonic acid monohydrate | 0.042 | 110 | 120 | 52 | 7.7 |
| Tetradecanol | Ti(OC$_4$H$_9$)$_4$ | 0.3 | 90 | 120 | >99 | 5.4 |
| Tetradecanol | Ti(OC$_4$H$_9$)$_4$ | 0.15 | 90 | 120 | >99 | 4.8 |

TABLE 5-continued

| Alcohol | Catalyst | Quantity of catalyst (in each case equimolar) in g | Temperature °C. | Time min | Transesterification conversion (4 OR' = 100%) | Quantity of oligomers (comparison of integrals from Si NMR, Si(OR)$_3$ = 100%; oligomers = x %) |
|---|---|---|---|---|---|---|
| Tetradecanol | Ti(OC$_4$H$_9$)$_4$ | 0.075 | 90 | 120 | 91 | 4.7 |
| Tetradecanol | p-toluenesulfonic acid monohydrate | 0.168 | 90 | 120 | >99 | 5.9 |
| Tetradecanol | p-toluenesulfonic acid monohydrate | 0.084 | 90 | 120 | 85 | 6.3 |
| Tetradecanol | p-toluenesulfonic acid monohydrate | 0.042 | 90 | 120 | 49 | 5.5 |

TABLE 6

| Alcohol | Catalyst | Quantity of catalyst in g | Temperature (°C.) | Time (min) | Transesterification conversion (4 OR' = 100%) | Quantity of oligomers (comparison of integrals from Si NMR, R'Si(OR)$_3$ = 100, oligomers = x) |
|---|---|---|---|---|---|---|
| Dodecanol | Ti(OC$_4$H$_9$)$_4$ | 0.5 | 130 | 120 | >99 | 8.7 |
| Tetradecanol | Ti(OC$_4$H$_9$)$_4$ | 0.5 | 130 | 120 | >99 | 8 |
| Diethylene glycol monobutyl ether | Ti(OC$_4$H$_9$)$_4$ | 0.5 | 130 | 120 | >99 | 6.9 |
| Dodecanol | Ti(OC$_3$H$_7$)$_4$ | 0.5 | 130 | 120 | >99 | 10.3 |
| Tetradecanol | Ti(OC$_3$H$_7$)$_4$ | 0.5 | 130 | 120 | >99 | 9.3 |
| Diethylene glycol monobutyl ether | Ti(OC$_3$H$_7$)$_4$ | 0.5 | 130 | 120 | >99 | 11 |
| Dodecanol | Ti(OC$_2$H$_5$)$_4$ | 0.5 | 130 | 120 | >99 | 7.7 |
| Tetradecanol | Ti(OC$_2$H$_5$)$_4$ | 0.5 | 130 | 120 | >99 | 8.7 |
| Diethylene glycol monobutyl ether | Ti(OC$_2$H$_5$)$_4$ | 0.5 | 130 | 120 | >99 | 10.5 |
| Dodecanol | Toluenesulfonic acid, Na salt C$_7$H$_7$NaO$_3$S | 0.5 | 130 | 120 | 52 | 4.7 |
| Tetradecanol | Toluenesulfonic acid, Na salt C$_7$H$_7$NaO$_3$S | 0.5 | 130 | 120 | 53 | 4.8 |
| Diethylene glycol monobutyl ether | Toluenesulfonic acid, Na salt C$_7$H$_7$NaO$_3$S | 0.5 | 130 | 120 | 52 | 4.8 |

Modifications and Other Embodiments

Various modifications and variations of the described compositions and their methods of use as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the chemical, chemical engineering, biochemical, industrial or related fields are intended to be within the scope of the following claims.

Incorporation by Reference

Each document, patent, patent application or patent publication cited by or referred to in this disclosure is incorporated by reference in its entirety. However, no admission is made that any such reference constitutes prior art and the right to challenge the accuracy and pertinency of the cited documents is reserved. Specifically, priority documents DE (Germany) 101 37 809.2, filed Aug. 6, 2001, DE 101 63 941.4, filed Dec. 22, 2001, and DE 102 23 073.0, filed May 24, 2002, are hereby incorporated by reference.

The invention claimed is:

1. Organosilicon compounds of formula I and/or II

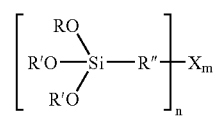

I

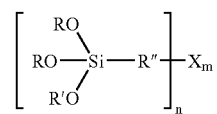

II wherein
R is a methyl or ethyl group, with the proviso that R is ethyl when X is SH,
R' is identical or different and is a C$_9$-C$_{30}$ branched or unbranched monovalent alkyl or alkenyl group, aralkyl group, branched or unbranched C$_2$-C$_{30}$ alkyl ether group, branched or unbranched C$_2$-C$_{30}$ alkyl polyether group or R'''₃Si, where R''' is $C_1$-$C_{30}$ branched or unbranched alkyl or alkenyl group, aralkyl group or aryl group, R'' is a branched or unbranched, saturated or unsaturated, aliphatic, aromatic or mixed aliphatic/aromatic divalent $C_1$-$C_{30}$ hydrocarbon group, and X is O(C=O)—R''' where n=1 and m=1, SH where n=1 and m=1, S where n=2 and m=1-10 and mixtures thereof or S(C=O)—R''' where n=1 and m=1, with the proviso that in formula I, when m=4 and n=2, R can not be ethyl, R' can not be $C_{14}H_{29}$ and R'' can not be —(CH₂)₃— or —(CH₂)₄— and with the proviso that in formula II, when m=4, n=2, R is ethyl, and R'' is —(CH₂)₃—, R' when monovalent alkyl, is $C_{12}$-$C_{30}$-branched or unbranched monovalent alkyl.

2. The organosilicon compounds of claim 1 of formula (I).

3. The organosilicon compounds of claim 1 of formula (II).

4. The organosilicon compounds of claim 1, wherein R'' is CH₂, CH₂CH₂, CH₂CH₂CH₂, CH₂CH₂CH₂CH₂, CH(CH₃), CH₂CH(CH₃), C(CH₃)₂, CH(C₂H₅), CH₂CH₂CH(CH₃), CH₂CH(CH₃)CH₂ or

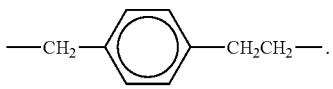

5. A composition comprising one or more organosilicon compounds of claim 1, which may be free, bonded or crosslinked.

6. A rubber or synthetic rubber comprising one or more organosilicon compounds of claim 1, which may be free, bonded or crosslinked.

7. The rubber or synthetic rubber of claim 6, wherein the organosilicon compound is bonded or crosslinked.

8. The rubber or synthetic rubber of claim 6 that comprises rubber or synthetic rubber, filler, and optionally one or more rubber auxiliary substance(s).

9. The rubber or synthetic rubber of claim 6 comprising one or more carbon black(s).

10. The rubber of claim 6 comprising one or more highly dispersed silica(s).

11. The rubber of claim 6 comprising one or more silica(s).

12. The rubber of claim 6 comprising one or more aluminum oxides or aluminum hydroxides.

13. The rubber of claim 6 comprising one or more glass fibres, glass fibre products or glass microbeads.

14. A synthetic rubber comprising the organosilicon compound of claim 1.

15. A natural rubber comprising the organosilicon compound of claim 1.

16. A moulding comprising the organosilicon compound of claim 1.

17. A tire, pneumatic tire or tire tread comprising the organosilicon compound of claim 1.

18. Cable sheathing comprising the organosilicon compound of claim 1.

19. A hose, drive belt, conveyor belt, roll cover, shoe sole, sealant ring or damping component comprising the compound of claim 1.

20. A method for producing a rubber or synthetic rubber mixture comprising admixing one or more organosilicon compound(s) of claim 1 with rubber or synthetic rubber, with a rubber auxiliary or with a compound to be added to a rubber mixture.

21. The method of claim 20, wherein the amount of the organosilicon compound(s) relative to the weight of said rubber ranges from 0.1% to 20 wt %.

22. A method for promoting adhesion between an inorganic material and an organic polymer comprising contacting the organosilicon compound of claim 1 with an inorganic material and an organic polymer.

23. The method of claim 22, wherein the inorganic material comprises glass.

24. The method of claim 22, wherein the inorganic material comprises metal.

25. The method of claim 22, wherein the inorganic material comprises an oxide.

26. The method of claim 22, wherein the inorganic material comprises silica.

27. The method of claim 22, wherein the organic polymer comprises a thermoset polymer.

28. The method of claim 22, wherein the organic polymer comprises a thermoplastic polymer.

29. The method of claim 22, wherein the organic polymer comprises an elastomer.

30. A method for crosslinking one or more material(s) comprising contacting one or more material(s) with the organosilicon compound of claim 1.

31. A method for modifying the surface of a material, comprising contacting a surface with the organosilicon compound of claim 1.

32. A process for the production of the organosilicon compound of claim 1, comprising reacting a silane of formula III $$\left[ \begin{array}{c} RO \\ RO-Si-R'' \\ RO \end{array} \right]_n X_m \quad \text{III}$$

in which R, R'', X, m and n have the above-stated meanings, with one or more alcohol(s) of formula R'—OH, in which R' has the above-stated meaning, and eliminating R—OH.

33. The process of claim 32, wherein eliminating R—OH comprises continuous separation of R—OH from the reaction mixture by distillation.

34. The process of claim 32, comprising reacting the silane in the presence of a catalyst that is hydrochloric acid, sulfuric acid, phosphoric acid, formic acid, acetic acid, para-toluenesulfonic acid, sodium hydroxide solution, potassium hydroxide solution, sodium methylate or sodium ethylate.

35. The process of claim 32, comprising reacting the silane in the presence of catalyst that is a metal compound.

36. The process of claim 32, comprising reacting the silane at a temperature of between 20 and 200° C.

37. The process of claim 32, comprising reacting the silane in an anhydrous, inert gas atmosphere.

* * * * *